(12) United States Patent  (10) Patent No.: US 8,744,772 B1
Magro et al.  (45) Date of Patent: Jun. 3, 2014

(54) METHOD FOR SOIL ANALYSIS

(75) Inventors: Carmen Magro, King of Prussia, PA (US); Jeffrey Campbell, Boise, ID (US)

(73) Assignee: Green Badge, LLC, King of Prussia, PA (US)

( * ) Notice: Subject to any disclaimer, the term of this patent is extended or adjusted under 35 U.S.C. 154(b) by 764 days.

(21) Appl. No.: 12/911,720

(22) Filed: Oct. 25, 2010

Related U.S. Application Data

(60) Provisional application No. 61/255,073, filed on Oct. 26, 2009.

(51) Int. Cl.
*G01V 3/12* (2006.01)

(52) U.S. Cl.
USPC .................................. 702/2; 702/22; 702/128

(58) Field of Classification Search
USPC .................. 702/2, 22, 128; 436/183; 210/634; 73/863
See application file for complete search history.

(56) References Cited

U.S. PATENT DOCUMENTS

| | | | |
|---|---|---|---|
| 4,256,133 A | 3/1981 | Coward et al. | |
| 4,396,149 A | 8/1983 | Hirsch | |
| 4,684,920 A | 8/1987 | Reiter | |
| 4,785,843 A | 11/1988 | Nicholson | |
| 5,839,660 A | 11/1998 | Morgenstern et al. | |
| 6,754,298 B2 * | 6/2004 | Fessler | 378/4 |
| 6,937,939 B1 | 8/2005 | Shibusawa et al. | |
| 6,947,810 B2 | 9/2005 | Skinner | |
| 6,963,205 B2 | 11/2005 | Lundstrom et al. | |
| 7,063,270 B2 | 6/2006 | Bowers et al. | |
| 7,184,892 B1 | 2/2007 | Dyer et al. | |
| 7,264,177 B2 | 9/2007 | Buck et al. | |
| 7,318,010 B2 | 1/2008 | Anderson | |
| 7,413,380 B2 | 8/2008 | Corwon et al. | |
| 7,671,336 B2 * | 3/2010 | Jahn et al. | 250/339.11 |
| 2007/0237583 A1 | 10/2007 | Corwon et al. | |
| 2009/0099701 A1 | 4/2009 | Li et al. | |
| 2009/0276102 A1 | 11/2009 | Smith et al. | |
| 2010/0194411 A1 | 8/2010 | Caron | |

\* cited by examiner

*Primary Examiner* — Elias Desta
(74) *Attorney, Agent, or Firm* — Clause Eight IPS; Michael Catania

(57) ABSTRACT

A method for soil analysis for determining optimal conditions for a soil area and reporting the same. The soil analysis of the present invention combines sound agronomic principles with a unique interpretation of the results to offer a thorough analysis of a property's soil based on the soil sample(s) taken from a particular property. The calculation formulas and variables are consistent for all analyses, with the formulas adjusted based on some specific qualities of the soil.

20 Claims, 6 Drawing Sheets

| Property & Sample Information | | Physical | | Exchangeable (ppm) | | Extractable (Available) | | |
|---|---|---|---|---|---|---|---|---|
| Property | | | | Nutrient | ppm | Nutrient | meq/L | ppm |
| Property | CARD SOUND GC | pH | 7.2 | NO3 | 5 | NO3 | | 5.04 |
| Sample ID | 10GRN | Buffer pH | 0 | P | 21 | NH4 | | 8.40 |
| Date of Sample | 13-Jul-09 | OM % | 3.6 | Ca | 500 | PO4 | | 8.14 |
| Lab ID | 9283987 | CEC | 3.6 | Mg | 69 | Ca | 1.2 | 24.05 |
| | | Texture | SAND | K | 125 | Mg | 0.59 | 7.17 |
| | | Sand | 96% | S | 16 | K | 1.25 | 48.88 |
| | | Silt | 2 % | Fe | 31.5 | SO4 | | 69.60 |
| | | Clay | 2 % | Mn | 3.2 | BO3 | | 0.33 |
| | | Saturation % | 42.86 | Zn | 16 | Na | 1.09 | 25.07 |
| | | SAR | 1.15 | Cu | 1.1 | Cl | | 58.10 |
| | | EC (1:1 Sol. Salts) | 0.16 | B | 0.6 | HCO3 | | 62.83 |
| | | EC (Paste Extract) | 0.53 | Na | 36 | TOT | | 317.60 |
| | | | | TOT | 824.4 | | | |

| Base Saturation % | | Potential Base % | | Available Base % | | Ratios | | |
|---|---|---|---|---|---|---|---|---|
| Nutrient | % of CE | Nutrient | % of CE | Nutrient | % of Tot | | Exch. | Extr. |
| Ca | 70.4 | Ca | 68.49 | Ca | 22.87 | Nutrients + Salts | | |
| Mg | 16.2 | Mg | 9.45 | Mg | 6.82 | NO3/NH4 | | 0.60 |
| K | 9 | K | 17.12 | K | 46.47 | Ca/Mg | 7.25 | 3.35 |
| Na | 4.4 | Na | 4.93 | Na | 23.84 | N/K | 0.04 | 0.27 |
| H | 0 | | | | | Ca/P | 23.81 | 2.96 |
| | | | | | | (Na-Cl-HCO3)/Tot. | | 0.27 |
| | | | | | | Ca/HCO3 | 7.96 | 0.38 |
| | | | | | | Mg/HCO3 | 1.10 | 0.11 |
| | | | | | | K/Cl | 2.15 | 0.84 |
| | | | | | | Tot. Extr./Tot. Exch. Salts | | 0.39 |

FIG. 2

| Physical Report | | Exchangeable Report | | Extractable (Available) Report | |
|---|---|---|---|---|---|
| Variable | LOG Value | Variable | LOG Value | Variable | LOG Value |
| pH | 122.21 | NO3 | 5.00 | NO3 | 5.00 |
| Buffer pH | 122.21 | P | 5.00 | NH4 | 62.23 |
| OM % | 138.29 | Ca | 39.79 | PO4 | 5.00 |
| CEC | 121.39 | Mg | 35.50 | Ca | 5.00 |
| Texture | SAND | K | 39.79 | Mg | 5.00 |
| Sand | 0.96 | S | 80.62 | K | 86.64 |
| Silt | 0.02 | Fe | 8.81 | SO4 | 83.26 |
| Clay | 0.02 | Mn | 5.00 | BO3 | 90.98 |
| Saturation % | 186.89 | Zn | 80.62 | Na | 116.00 |
| SAR | 109.10 | Cu | 5.00 | CL | 123.16 |
| EC (1:1 Sol. Salts) | 100.00 | B | 77.82 | HCO3 | 116.05 |
| EC (Paste Extract) | 100.00 | Na | 135.78 | TOT. AVAIL. SALTS | 53.35 |
|  |  | TOT. POT. SALTS | 5.00 |  |  |

| Base Saturation % Report | | Potential Base % Report | | Available Base % Report | | Ratio Report | |
|---|---|---|---|---|---|---|---|
| Variable | LOG Value | Variable | LOG Value | Variable | LOG Value | Variable | LOG Value |
| Ca | 106.45 | Ca | 97.16 | Ca | 5.00 | NO3/NH4 | 5.00 |
| Mg | 101.62 | Mg | 16.08 | Mg | 5.00 | Ca/Mg | 42.48 |
| K | 152.83 | K | 199.15 | K | 200.00 | N/K | 5.00 |
| Na | 173.65 | Na | 200.00 | Na | 200.00 | Ca/P | 63.48 |
| H | 5.00 |  |  |  |  | (Na-Cl-HCO3)/Tot. | 127.23 |
|  |  |  |  |  |  | Ca/HCO3 | 5.00 |
|  |  |  |  |  |  | Mg/HCO3 | 5.00 |
|  |  |  |  |  |  | K/Cl | 49.76 |
|  |  |  |  |  |  | TOT. Potential/ TOT. Available Salts | 96.74 |

FIG. 3

| | Nutrient/Variable | Analysis |
|---|---|---|
| | SAMPLE REPORT<br>UgMO Soil Analysis<br>10GRN<br>July 13, 2009 | |
| Physical and Chemical | pH<br>Organic Matter<br>CEC<br>Saturation % | pH is alkaline and affecting the availability of several ... |
| Potential Nutrients and Salts | NO3<br>P<br>Ca<br>Mg<br><br>Total Potential Salts | Soil exchangeable Nitrate is very low. Consider build ... |
| Available Nutrients and Salts | NO3<br>NH4<br>PO4<br>Ca<br><br>Total Available Salts | Soil available Nitrate is very low. Consider building ... |
| Potential Base Saturation | Ca PBS<br>Mg PBS<br>K PBS | % Base Saturation of Calcium is acceptable. |
| Available Base % | Available Ca Base %<br>Available Mg Base % | Available base % of Calcium is very low. Routine ... |
| Ratio Analyses | NO3/NH4<br>Ca/Mg | Available ratio of Nitrate to Ammonia is very low ... |

FIG. 5

METHOD FOR SOIL ANALYSIS

CROSS REFERENCE TO RELATED APPLICATION

The Present Application claims priority to U.S. Provisional Patent Application No. 61/255,073, filed on Oct. 26, 2009, which is hereby incorporated by reference in its entirety.

STATEMENT REGARDING FEDERALLY SPONSORED RESEARCH OR DEVELOPMENT

Not Applicable

BACKGROUND OF THE INVENTION

1. Field of the Invention

The present invention relates to a method for soil analysis. More specifically, the present invention relates to a method for soil analysis for determining optimal conditions for a soil area and reporting the same.

2. Description of the Related Art

The prior art discloses various soil analysis methods and means for communicating the analysis to an individual such as a land owner.

The industry standard for soil testing involves similar ways of taking soil samples for most of the time. This requires random samples to be taken from an area using a standard soil sampling tool, submitting those samples to the lab and then having them analyzed. Once analyzed, the results are given in data format showing many variables with numbers where the user is left to interpret much of the report. Some labs will offer a weighted value for certain variables with limited interpretation of the results.

BRIEF SUMMARY OF THE INVENTION

The present invention provides a solution to the problems of the prior art.

The soil analysis of the present invention combines sound agronomic principles with a unique interpretation of the results to offer a thorough analysis of a property's soil based on the soil sample(s) taken from a particular property. The calculation formulas and variables are consistent for all analyses, with the formulas adjusted based on some specific qualities of the soil.

The present invention requires the soil samples to be between 3 and 4 inches for turfgrass so that the active root-zone medium that is most influential on salt and soil qualities within the profile are examined. The present invention also requires that the "cap" or component of the sample core that has the grass on it remains intact so that the lab can consistently remove the cap properly to truly measure the soil qualities. Finally, the present invention applies a unique logarithmic equation with varying slopes to account for every variable the lab reports plus additional variables and ratios that are important for plant and soil management. The slopes vary for each variable to accommodate the "buffer" allowance or tolerance level of being farther away from what is ideal. The ideal, or nominal value for each variable is based on scientific fact, observations and the inventors' experience.

A default slope of 20 is used in the algorithmic equations unless an otherwise more appropriate slope is used for each variable. The slope dictates the strength or intensity of the change in calculated logarithmic value as the actual recorded value strays away from the optimal value. The index value (scale) is another number used in the logarithmic equation to place all values on a logarithmic scale of 100 for easy scaling of very different variables.

One aspect of the present invention is a method for analyzing soil conditions for a land area. The method includes analyzing at least one soil sample for a land area, the soil sample ranging from 3 inches to 4 inches and including a cap. The method also includes generating a plurality of variables for the at least one analyzed soil sample. The method also includes applying a logarithmic equation to each of the plurality of variables to generate a plurality of logarithmic values for the at least one soil sample.

The method optionally includes generating a plurality of ratios of variables for the at least one analyzed soil sample and applying a logarithmic equation to each of the plurality of ratios of variables to generate a plurality of logarithmic ratio values for the at least one soil sample.

The plurality of variables preferably comprises pH, buffer pH, organic matter %, texture, sand, silt, clay, saturation %, cation exchange capacity, sodium adsorption ratio, electrical conductivity soluble salts and electrical conductivity paste extract salts. The plurality of variables alternatively comprises a plurality of acid exchangeable nutrients and a plurality of free-extractable nutrients. The plurality of variables for the plurality of acid exchangeable nutrients preferably comprises nitrate, phosphorous, calcium, magnesium, potassium, sulfur, iron, manganese, zinc, copper, boron and sodium. The plurality of variables for the plurality of free extractable nutrients preferably comprises nitrate, ammonium nitrogen, phosphate, calcium, magnesium, potassium, sulfate, borate, sodium, chlorine and bicarbonate. The plurality of variables alternatively comprises a plurality of base saturation percentages, a plurality of potential base percentages, and a plurality of available base percentages. The plurality of variables for the plurality of base saturation percentages preferably comprises calcium base saturation percent, magnesium base saturation percent, potassium base saturation percent, sodium base saturation percent, and hydrogen base saturation percent. The plurality of variables for the plurality of potential base percentages preferably comprises calcium potential base percent, magnesium potential base percent, potassium potential base percent, and sodium potential base percent. The plurality of variables for the plurality of available base percentages preferably comprises calcium available base percent, magnesium available base percent, potassium available base percent, and sodium available base percent. Each of the plurality of logarithmic values is a value between 0 and 200. The optimal value for each of the plurality of logarithmic values is preferably a value between 80 and 120.

The plurality of ratios of variables preferably comprises available nitrate to ammonium nitrogen, available calcium to magnesium, available nitrogen to potassium, available calcium to phosphorus, total of sodium, chlorine and bicarbonates to the total available salts in solution, available calcium to bicarbonates, available magnesium to bicarbonates, available potassium to chlorides, and total potential exchangeable salts to total available extractable salts.

Each of the plurality of logarithmic ratio values is preferably a value between 0 and 200.

Another aspect of the present invention is a method for determining optimal soil values for a land area. The method includes analyzing at least one soil sample for a land area. The method also includes generating a plurality of variables based on the at least one analyzed soil sample. The method also includes applying a logarithmic equation to each of the plurality of variables to generate a plurality of logarithmic values for the at least one soil sample. The method also includes determining a plurality of optimal soil values for the land area. The method optionally includes generating a plurality of ratios of variables for the at least one analyzed soil sample and applying a logarithmic equation to each of the plurality of ratios of variables to generate a plurality of logarithmic ratio values for the at least one soil sample. The method optionally includes analyzing a plurality of soil samples of the land area to generate the plurality of variables.

Yet another aspect of the present invention is a method for analyzing soil conditions for a land area. The method includes analyzing a plurality of soil samples for a land area, each of the plurality of soil samples ranging from 3 inches to 4 inches and including a cap. The method also includes generating a plurality of variables for the analyzed plurality of soil samples. The method also includes applying a logarithmic equation to each of the plurality of variables to generate a plurality of logarithmic values for the plurality of soil samples, wherein the logarithmic equation is logarithmic value=slope*LOG(actual variable value/optimal variable value)+scale. The method optionally includes generating a plurality of ratios of variables for the at least one analyzed soil sample and applying a logarithmic equation to each of the plurality of ratios of variables to generate a plurality of logarithmic ratio values for the at least one soil sample. The method optionally includes analyzing a plurality of soil samples of the land area to generate the plurality of variables.

The optimal value for the variable is preferably determined based on a plurality of factors comprising the type of soil, the climate, the average temperature, the amount of sunlight, the water amount, the ground temperature, the growing year, and the like. The type of soil preferably comprises the porosity of the soil. The plurality of factors further comprises evapotranspiration value for plants in the soil area, a relative humidity value for a soil area, and/or a soil degree day values.

Yet another aspect of the present invention is a method for analyzing soil conditions for a land area. The method includes analyzing a plurality of soil samples for a land area, each of the plurality of soil samples ranging from 3 inches to 4 inches and including a cap. The method also includes generating a plurality of variables and a plurality of ratios of variables for the analyzed plurality of soil samples. The method also includes applying a logarithmic equation to each of the plurality of variables and each of the plurality of ratios of variables to generate a plurality of logarithmic values for the plurality of soil samples, wherein the logarithmic equation is logarithmic value=slope*LOG(actual variable value/optimal variable value)+scale. Yet another aspect of the present invention is a report for determining optimal soil conditions for a land area. The report is generated by a method including analyzing a plurality of soil samples for a land area, each of the plurality of soil samples ranging from 3 inches to 4 inches and including a cap. The method also includes generating a plurality of variables and a plurality of ratios of variables for the analyzed plurality of soil samples. The method also includes applying a logarithmic equation to each of the plurality of variables and each of the plurality of ratios of variables to generate a plurality of logarithmic values for the plurality of soil samples, wherein the logarithmic equation is logarithmic value=slope*LOG(actual variable value/optimal variable value)+scale.

Yet another aspect of the present invention is a method for analyzing soil conditions for a land area. The method includes analyzing at least one soil sample for a land area. The method also includes generating a plurality of variables for the at least one analyzed soil sample. The method also includes applying a scaling function to each of the plurality of variables to generate a plurality of scaled variable values for the at least one soil sample.

Yet another aspect of the present invention is a method for analyzing soil conditions for a land area. The method includes analyzing at least one soil sample for a land area. The method also includes generating a plurality of variables for the at least one analyzed soil sample. The method also includes applying a scaling function to each of the plurality of variables to generate a plurality of scaled variable values for the at least one soil sample, wherein such that for each variable value $V_1, \ldots V_n$, then $S_1=f_1(V_1) \ldots S_n=f_n(V_n)$, wherein $S_1 \ldots S_n$ are scaled variable values and $f_1 \ldots f_n$ are functions specific to each variable $V_1 \ldots V_n$.

Yet another aspect of the present invention is a method for analyzing soil conditions for a land area. The method also includes obtaining at least one soil sample from a land area. The method also includes analyzing the at least one soil sample for the land area. The method also includes generating a plurality of variables for the at least one analyzed soil sample. The method also includes applying a scaling function to each of the plurality of variables to generate a plurality of scaled variable values for the at least one soil sample.

The land area preferably comprises at least one crop type selected from vineyards, nuts, potatoes, sugarcane, avocados and alfalfa.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 2 is a table of the nominal values for a sample analysis.

FIG. 3 is a table of the logarithmic values for a sample analysis.

FIG. 5 is a table of a summary of the analysis of each variable for a sample analysis.

DETAILED DESCRIPTION OF THE INVENTION

Figure 1:
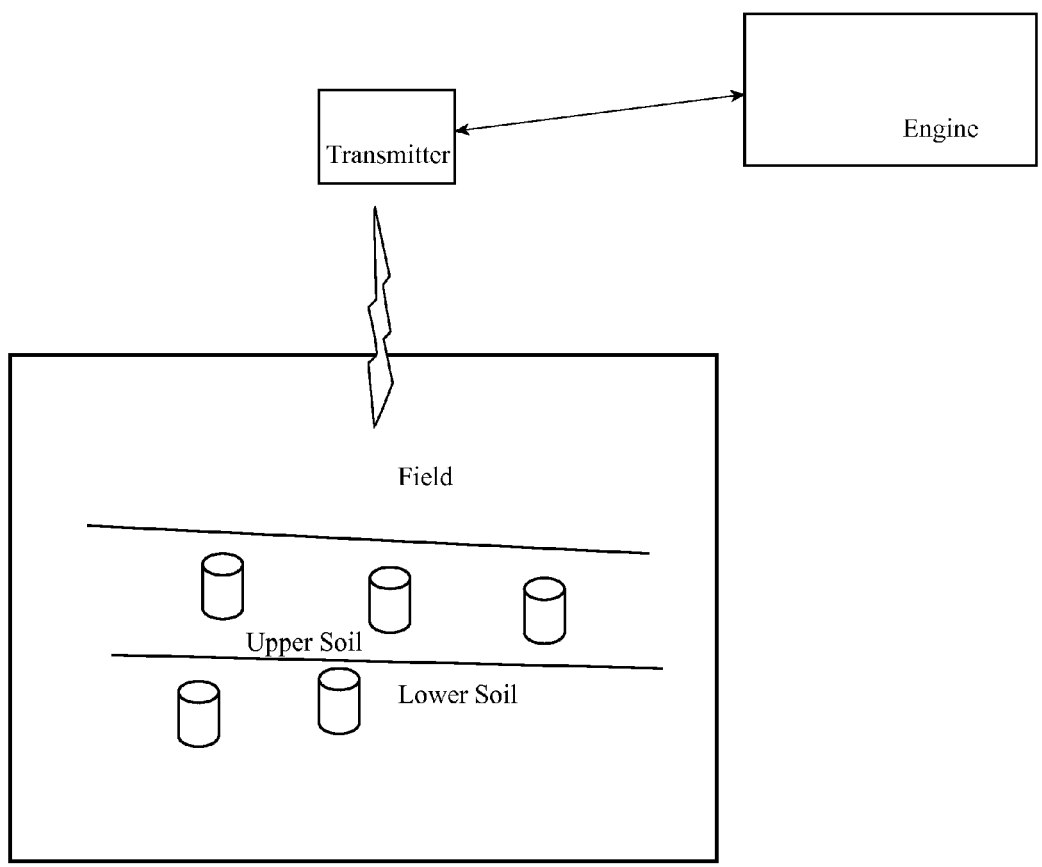
FIG. 1 is a schematic diagram of a system for monitoring a land area.
Figure 4:
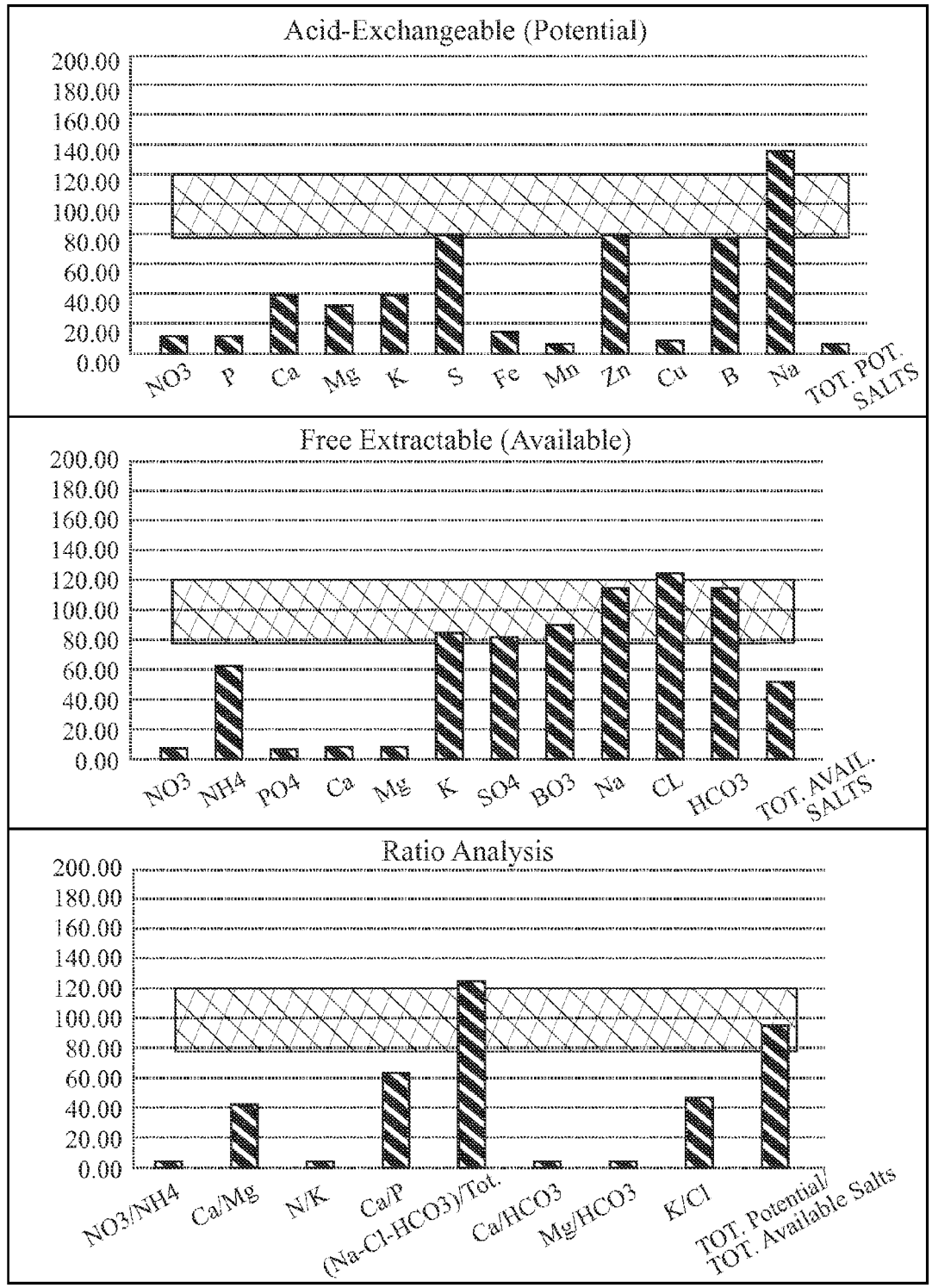
FIG. 4 is a collection of graphs of the logarithmic values for a sample analysis.
Figure 4A:
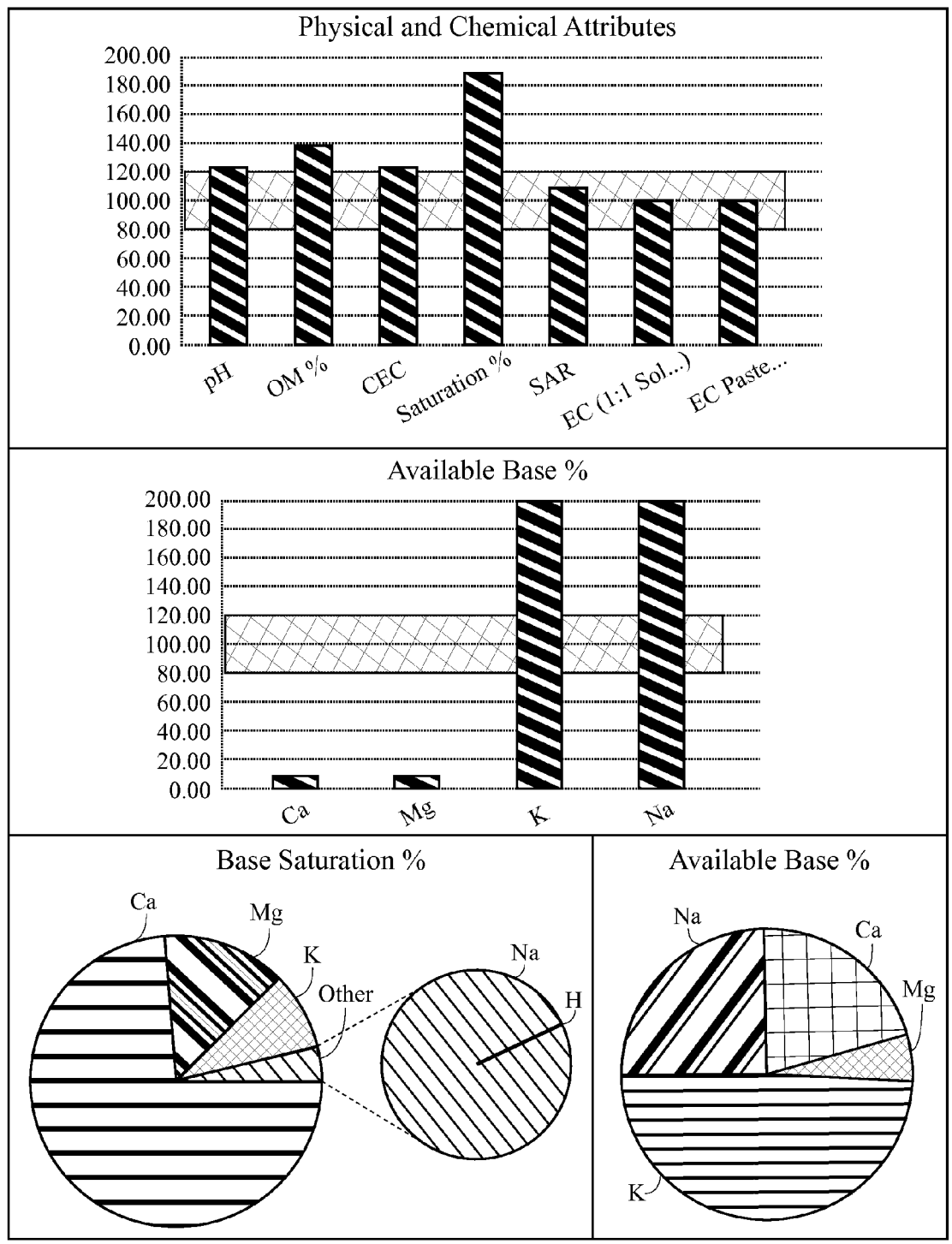
FIG. 4A is a collection of graphs of the logarithmic values for a sample analysis.

As shown in FIG. 1, a system for monitoring a land area either prior or subsequent to the analysis is generally designated 20. Such a system is disclosed in Glancy, et al., U.S. Patent Publication Number 2006/0178847 for an Apparatus And Method For Wireless Real Time Measurement And Control Of Soil And Turf Conditions, which is hereby incorporated by reference in its entirety.

Such a system is preferably used with a system, sensor and method such as disclosed in Campbell, U.S. Pat. No. 7,482,820 for a Sensor For Measuring Moisture And Salinity, which is hereby incorporated by reference in its entirety. Other components are disclosed in U.S. patent application Ser. No. 12/697,256, filed on Jan. 31, 2010 for a Method And System For Soil And Water Resources, which is hereby incorporated by reference in its entirety. Other components are disclosed in U.S. patent application Ser. No. 12/697,257, filed on Jan. 31, 2010 for a Method And System For Soil And Water Resources, which is hereby incorporated by reference in its entirety. Other details of sensors are as disclosed in Campbell, U.S. Pat. No. 7,482,820 for a Sensor For Measuring Moisture And Salinity, which is hereby incorporated by reference in its entirety. An additional sensor and irrigation system is disclosed in Campbell et al., U.S. patent application Ser. No. 12/697,254 for a Method And System For Soil And Water Resources, filed on Jan. 31, 2010, which is hereby incorporated by reference in its entirety, and the non-provisional patent application of this provisional patent application, which is Campbell et al., for a Method And System For Monitoring Soil And Water Resources, U.S. patent application Ser. No. 12/698,176, filed on Feb. 2, 2010, and hereby incorporated by reference in its entirety.

Various monitoring techniques are disclosed in U.S. patent application Ser. No. 12/697,292, filed on Jan. 31, 2010 for a Wireless Soil Sensor Utilizing A RF Frequency For Performing Soil Moisture Measurements, which is hereby incorporated by reference in its entirety. Other Various monitoring techniques are disclosed in U.S. patent application Ser. No. 12/698,138, filed on Feb. 1, 2010 for a Method, System And Sensor For Performing Soil Measurements, which is hereby incorporated by reference in its entirety. Other Various monitoring techniques are disclosed in U.S. patent application Ser. No. 12/697,226, filed on Jan. 30, 2010 for a Method And System For Monitoring Soil And Water Resources, which is hereby incorporated by reference in its entirety. Other Various monitoring techniques are disclosed in U.S. patent application Ser. No. 12/697,283, filed on Jan. 31, 2010 for an Adaptive Irrigation Control, which is hereby incorporated by reference in its entirety. Other Various monitoring techniques are disclosed in U.S. patent application Ser. No. 12/697,281, filed on Jan. 31, 2010 for an Irrigation Interrupter, which is hereby incorporated by reference in its entirety.

FIGS. 2-5 illustrate sections of an analysis report which is provided to an individual associated with a land area to communicate the soil conditions of the land area and also to communicate optimal soil conditions for the land area.

The land area is analyzed to determine optimal conditions for that particular land area. Various features make a land area unique. One such feature is the composition of the soil, or the soil profile. Sand is the texture that allows for the most macro, or large pore spaces allowing for very free movement of water and nutrients through the soil profile. A clay soil allows for the least amount of free water movement through the soil profile even though it has much more pore space. The pore space in the clay soil however is very small and considered micro pore space. These pores hold onto water tightly and limit oxygen, root growth and other key qualities necessary for strong plant health. All other textures lie incrementally between sand and clay. From largest macro pore space to smallest, the twelve agronomic documented textural classifications are Sand, Loamy Sand, Sandy Loam, Loam, Silt Loam, Silt, Sandy Clay Loam, Clay Loam, Silty Clay Loam, Sandy Clay, Silty Clay, and Clay. These textural classifications are typically referenced in a soil report and determined based on the percentages of sand, silt and clay in the soil profile.

Organic Matter (OM) % which is another physical component of soil varies greatly from site to site and around a particular site. Also, OM % changes throughout a growing year. Knowing what the OM % is will allow further analysis of how likely a soil is to have water/air relationship problems or other physical issues that affect plant and soil health as well as surface conditions and performance. For every soil texture there is an ideal organic matter percentage which is based on professional and educational experience. A very important consideration of OM % is that it can greatly change the fundamental quality of a type of soil texture. For instance, a sand, which again has very large pores for free water movement, with higher than optimal organic matter % can very easily act like a clay or limit water and air movement. This oftentimes occurs near the surface so that qualities in the top few inches of the soil behave quite differently than the soil beneath it. This adds to the value of placing monitoring sensors precisely at the depths of most importance from site to site.

Cation Exchange Capacity (CEC) is a lab based measurement that uses extracted nutrients to determine how many nutrients a soil can hold. It is influenced primarily by soil texture and organic matter %. The higher the CEC, the more water and nutrients a soil can hold so it is a good indication of soil health. While a higher CEC indicates more nutrients in the soil, it also indicates that if we are holding a lot of nutrients, we have a high likelihood that moisture and nutrients may not move very well through the entire profile. While this value could be considered as a tell-all for the entire profile, it isn't. Since turfgrass is a large organic matter producer, the CEC changes at different layers in the soil profile due to the abundance of growth near the surface and not so much in deeper parts of the soil. Agricultural properties that have crops with variable root depths have quite a different soil quality than turfgrass as the organic zone is not limited to the top couple of inches.

The CEC inequality is particularly true in sandy soils which are often found on turfgrass properties. OM % comes from organic acids that exude from the plant's roots and underground stems. This acid and deteriorating plant matter continuously add to the organic matter buildup and accumulate primarily in the upper soil profile. If the organic matter and CEC qualities are distributed equally throughout a soil which is not often the case, then the qualities of the soil are healthier since we have similar physical soil qualities throughout the profile to allow for water attracting itself to the consistent soil components. Water will move in all directions in the soil when it has these components to attract to. However, when the water holding qualities in one part differ from those in another part of the soil, one gets quite different reactions to water and nutrients. Therefore, Texture, Organic Matter % and CEC all have to be considered when identifying the optimal values for each.

Saturation Index % is a measurement at the lab that determines how many equal parts of water a soil sample will take to be saturated. Saturation is measured by knowing the precise point that the soil is holding as much water as it possible can. In other words, if any more water was introduced, it would drain out of the soil sample. So with 100 parts of soil (typically measured in grams) and the Saturation Index % is 25.1, indicates that it takes 25.1 equal parts of water (usually measured in mL) to saturate the 100 grams of soil. The Saturation Index % optimal values change depending on the soil type primarily. However, the CEC should be considered as well since all of these physical variables influence each other.

The soil solution contains several salts that consist of positively charged ions (cations) and negatively charged ions (anions). Some of these are beneficial and some are detrimental. When the total quantities of the individual salts are excessive, whether beneficial or not, the turfgrass plants and/or soil experience exponentially detrimental effects. However, detrimental salts can be detrimental at very low quantities while very low levels of beneficial salts may or may not be detrimental depending on the optimal values.

The potential base % report takes each Exchangeable (parts per million (ppm)) variable of Ca, Mg, K and Na and compares it to the total of these four values combined to get the percentage of each to the total. We then take that number and use our optimal value for calculating the logarithmic value. The same is true for the Available Base % Report except that we use the Extractable (Available) Report values instead of the Exchangeable (ppm) values. The Ratio Report is invented and shown to illustrate key correlations in the soil. All values are derived using the Extractable (Available) values in the lab analysis. For instance, the (Na—CI—HC03)/Tot ratio value takes the extractable values of Sodium (Na), Chlorine (CI) and Bicarbonates (HC03) which are considered poor salts in the soil and then divides them into the total of all available salts to get a percentage of bad salts occupying the total salt content. The logarithmic value then references the optimal value to calculate the value of this relationship in this soil test.

The analysis of physical and chemical equations includes the following.

pH:=IF(AND(AK8<121,AK8>79), pH is optimum for most nutrient availability and uptake. IF(AND(AK8>60, AK8<80), pH is significantly acidic and affecting the routine availability of calcium and the balance of other nutrients. Consider amendments to raise pH. Balance all nutrient inputs to allow for most benefit to the turf 1,IF(AK8<60, pH is extremely acidic. Consider aggressive modifications and products to raise pH and allow for more nutrient availability from soil resources. Calcium inefficiencies are likely. Balance all nutrient inputs to allow for most benefit to the turf, IF(AND(AK8>120,AK8<141), pH is alkaline and affecting the availability of several nutrients, particularly Iron, Manganese and Zinc. Balance all nutrient inputs to allow for most benefit to the turf, IF(AK8>140, pH is extremely alkaline.

Organic Matter:=IF(AND(AK10<121,AK10>79),OM % is acceptable, IF(AND(AK10>60,AK10<80), OM % is limiting. Improve plant growth to introduce OM throughout the rootzone, IF(AK10<60,OM % is extremely low limiting nutrient and water holding capacity in the soil. Consider amendments to improve OM % rapidly and supplement nutrients regularly, IF(AND(AK10>120,AK10<141), OM % is significant. Consider cultural practices to remove or dilute OM and allow for more free oxygen and moisture movement throughout the soil, IF(AK10>140, OM % is extremely high. A severe reduction in plant root mass is likely as water and nutrients will be bound up in the OM-rich zone. Cultural practices are necessary to remove OM rapidly.

CEC:=IF(AND(AK11<121,AK11>79), CEC is optimum for your soil type, IF(AND(AK11>60,AK11<80),CEC is limiting for your soil. Improve OM % and supplement nutrients regularly, IF(AK11<60,CEC is extremely low. The ability for your soil to hold nutrients and water is extremely limiting. Consider amendments and frequent nutritional applications with supplemental soil applications, IF(AND (AK11>120,AK11<141), CEC is significant for your soil type. Watch your OM % closely and continue to remove or dilute it. CEC is directly related to water holding capacity, IF(AK11>140,"CEC is extremely high for your soil type. If this is consistent throughout the soil then that is good. Otherwise, consider amendments and cultural practices to control confined water and nutrient holding attributes.

Saturation %:=IF(AND(AK16<121,AK16>79)," Saturation % is acceptable for your soil, IF(AND(AK16>60, AK16<80),"Saturation percentage is low meaning that your soil has a limiting ability to hold water. Improve organic structure throughout your soil with amendments and improved plant growth depth, IF(AK16<60,"Saturation % is extremely limiting. Rapid loss of nutrients and water is likely. Consider amendments to improve this quality and supplement nutrients often, IF(AND(AK16>120,AK16<141), "Saturation % is significant resulting in the likelihood that your soil will hold water longer than optimum. Consider regular cultural practices to dry down the profile and move water deeper into the profile ",IF(AK16>140,"Saturation % is extreme. Your soil has limited to no ability to drain quickly enough for strong plant growth. Consider more aggressive cultural practices or drainage applications to amend and allow consistent water movement throughout the profile.

Sodium Adsorption Ratio (SAR):=IF(AND(AK17<121, AK17>79),"SAR is acceptable and Sodium is not a problem, IF(AND(AK17>60,AK17<80),"SAR is acceptable and Sodium is not a problem, IF(AK17<60,"SAR is acceptable and Sodium is not a problem, IF(AND(AK17>120, AK17<141),"SAR is significant and Sodium is high in relation to Calcium and Magnesium. Consider regular applications of soluble Calcium, Magnesium and Potassium. Improve drainage wherever possible, IF(AK17>140, SAR is extreme causing potential soil structure deterioration and rapid plant decline under stress. Improve drainage and consider routine applications of soluble base and other nutrients while limiting salt loads to low rates and frequent applications.

EC (1:1 Soluble Salts):=IF(AND(AK18<121,AK18>79), "Electrical conductivity in free solution is acceptable, IF(AND(AK18>60,AK18<80), Electrical conductivity in free solution is acceptable, IF(AK18<60,"Electrical conductivity in free solution is acceptable, IF(AND(AK18>120, AK18<141), Electrical conductivity is significant in free solution. Less tolerant grasses will show chlorotic tissue. Balance beneficial nutrients and insure proper drainage to prevent salt buildup, IF(AK18>140, Electrical conductivity is extreme in free solution. Stress is likely, particularly in salt-intolerant species. Insure good drainage and consider close intervals of light foliar and soil applications of beneficial nutrients and biostimulants.

EC Paste Extract:=IF(AND(AK19<121,AK19>79),"Electrical conductivity in the soil paste extract is acceptable, IF(AND(AK19>60,AK19<80), Electrical conductivity in the soil paste extract is acceptable, IF(AK19<60, Electrical conductivity in the soil paste extract is acceptable, IF(AND (AK19>120,AK19<141), Electrical conductivity is significant in the paste extract. Less tolerant grasses will show chlorotic tissue. Balance beneficial nutrients and insure proper drainage to prevent salt buildup ",IF(AK19>140, Electrical conductivity is extreme in free solution. Stress is likely, particularly in salt-intolerant species. Insure good drainage and consider close intervals of light foliar and soil applications of beneficial nutrients and biostimulants.

The potential nutrients and salts logarithmic equations includes the following.

N03:=IF(AND(AM8<121,AM8>79),"Soil exchangeable Nitrate is acceptable, IF(AND(AM8>60,AM8<80),"Soil exchangeable Nitrate is limiting. Consider foliar nitrogen applications routinely and build nitrogen reserves in soil while balancing other nutrients, IF(AM8<60,"Soil exchangeable Nitrate is very low. Consider building nitrogen reserves in the soil from organic sources of N and apply nitrogen regularly at light rates foliarly to prevent deficiencies while balancing other nutrients, IF(AND(AM8>120,AM8<141), "Soil exchangeable Nitrate is significant. Consider applications of complex amino acids to utilize nitrogen and prevent excessive tissue growth while balancing other nutrients. ",IF (AM8>140,"Soil exchangeable Nitrate is excessive. Regular applications of complex amino acids will help prevent succulent leaf growth. Limit nitrogen inputs and balance all other nutrients.

P:=IF(AND(AM9<121,AM9>79),"Soil exchangeable Phosphorus is acceptable, IF(AND(AM9>60,AM9<80), "Soil exchangeable Phosphorus is limiting. Consider foliar P applications and correct imbalances with soil applied nutrients, IF(AM9<60,"Soil exchangeable Phosphorus is very low. Consider building Phosphorus reserves in the soil from various sources of P and apply Phosphorus regularly at light rates foliarly to prevent deficiencies, IF(AND(AM9>120, AM9<141),"Soil exchangeable Phosphorus is significant. This may limit availability of other nutrients such as Calcium, Iron, Magnesium and Manganese. Improve balance in the soil to allow more nutritional benefit. ",IF(AM9>140,"Soil exchangeable Phosphorus is excessive. This is likely limiting the availability of other beneficial nutrients such as Ca, Mg, Fe and Mn. Balance all nutrient inputs to allow for most benefit to the turf.

Ca:=IF(AND(AM10<121,AM10>79),"Soil exchangeable Calcium is acceptable, IF(AND(AM10>60,AM10<80),"Soil exchangeable Calcium is limiting. Consider regular soil soluble Calcium applications and correct imbalances with soil applied nutrients, IF(AM10<60,"Soil exchangeable Calcium is very low. Regular applications of soil soluble Calcium are likely necessary for nutritional balancing in your soil, IF(AND(AM10>120,AM10<141),"Soil exchangeable Calcium is significant. This may limit availability of other nutrients. Improve balance in the soil to allow more nutritional benefit. ,IF(AM10>140, Soil exchangeable calcium is excessive. This is likely limiting the availability of other beneficial nutrients. Balance all nutrient inputs to allow for most benefit to the turf.

Mg:=IF(AND(AM11<121,AM11>79), Soil exchangeable Magnesium is acceptable, IF(AND(AM11>60,AM11<80), "Soil exchangeable Magnesium is limiting. Consider regular soil soluble Magnesium applications and correct imbalances with soil supplied nutrients, IF(AM11<60,"Soil exchangeable Magnesium is very low. Regular applications of soil soluble Magnesium are likely necessary for nutritional balancing in your soil, IF(AND(AM11>120,AM11<141),"Soil exchangeable Magnesium is significant. This may limit availability of other base nutrients, Phosphorus and, Zinc and disrupt efficient N uptake. Improve balance in the soil to allow more nutritional benefit, IF(AM11>140,"Soil exchangeable Magnesium is excessive. This is likely limiting the availability of several beneficial nutrients. Balance all nutrient inputs to allow for most benefit to the turf.

K:=IF(AND(AM12<121,AM12>79),"Soil exchangeable potassium is acceptable, IF(AND(AM12>60,AM12<80), "Soil exchangeable potassium is limiting. Consider regular soil soluble and foliar potassium applications and correct imbalances with soil applied nutrients, IF(AM12<60,"Soil exchangeable potassium is very low. Regular applications of soil soluble potassium and balancing nutritional inputs are likely necessary for improving plant health, IF(AND (AM12>120,AM12<141),"Soil exchangeable potassium is significant. This may limit availability of several other nutrients. Improve balance in the soil to allow more nutritional benefit and develop healthier turf ",IF(AM12>140,"Soil exchangeable potassium is excessive. This may limit the availability of other beneficial nutrients. Balance all nutrient inputs to allow for most benefit to the turf.

S:=IF(AND(AM13<121,AM13>79),"Soil exchangeable Sulfur is acceptable, IF(AND(AM13>60,AM13<80),"Soil exchangeable Sulfur is limiting. Consider regular soil soluble sulphate applications and correct imbalances with soil applied nutrients, IF(AM 13<60,"Soil exchangeable Sulfur is very low. Regular applications of soil soluble Sulfur and balancing nutritional inputs are likely necessary for improving plant health, IF(AND(AM13>120,AM13<141), Soil exchangeable Sulfur is significant. This may limit availability of several other nutrients. Improve balance in the soil to allow more nutritional benefit and develop healthier turf. ",IF (AM13>140,"Soil exchangeable Sulfur is excessive. This may limit the availability of other beneficial nutrients. Balance all nutrient inputs to allow for most benefit to the turf.

Fe:=IF(AND(AM14<121,AM14>79),"Soil exchangeable Iron is acceptable, IF(AND(AM14>60,AM14<80),"Soil exchangeable Iron is limiting. Consider regular soil soluble Iron applications and correct imbalances with soil applied and foliar nutrients, IF(AM14<60,"Soil exchangeable Iron is very low. Regular applications of soil soluble and foliar-applied Iron and balancing nutritional inputs are likely necessary for improving plant health, IF(AND(AM14>120, AM14<141), Soil exchangeable Iron is significant. This may limit availability of several other nutrients. Improve balance in the soil to allow more nutritional benefit and develop healthier turf, IF(AM14>140, Soil exchangeable Iron is excessive. This may limit the availability of other beneficial nutrients. Balance all nutrient inputs to allow for most benefit to the turf.

Mn:=IF(AND(AM15<121,AM15>79),"Soil exchangeable Manganese is acceptable, IF(AND(AM15>60, AM15<80),"Soil exchangeable Manganese is limiting. Consider regular soil soluble Manganese applications and correct imbalances with soil applied and foliar nutrients, IF(AM15<60,"Soil exchangeable Manganese is very low. Regular applications of soil soluble and foliar-applied Manganese and balancing nutritional inputs are likely necessary for improving plant health, IF(AND(AM15>120, AM15<141),"Soil exchangeable Manganese is significant. This may limit availability of several other nutrients. Improve balance in the soil to allow more nutritional benefit and develop healthier turf ,IF(AM15>140,"Soil exchangeable Manganese is excessive. This may limit the availability of other beneficial nutrients and cause toxicity effects. Balance all nutrient inputs to allow for most benefit to the turf.

Zn:=IF(AND(AM16<121,AM16>79), Soil exchangeable Copper is acceptable, IF(AND(AM16>60,AM16<80), Soil exchangeable Copper is limiting. Consider regular soil soluble Copper applications and correct imbalances with soil applied and foliar nutrients, IF(AM16<60,"Soil exchangeable Copper is very low. Regular applications of soil soluble and foliar-applied Copper and balancing nutritional inputs are likely necessary for improving plant health, IF(AND (AM16>120,AM16<141),"Soil exchangeable Copper is significant. This may limit availability of several other nutrients. Improve balance in the soil to allow more nutritional benefit and develop healthier turf ",IF(AM16>140,"Soil exchangeable Copper is excessive. This may limit the availability of other beneficial nutrients and cause toxicity effects. Balance all nutrient inputs to allow for most benefit to the turf.

Cu:=IF(AND(AM17<121,AM17>79),"Soil exchangeable Zinc is acceptable, IF(AND(AM17>60,AM17<80),"Soil exchangeable Zinc is limiting. Consider regular soil soluble Zinc applications and correct imbalances with soil applied and foliar nutrients, IF(AM17<60,"Soil exchangeable Zinc is very low. Regular applications of soil soluble and foliar-applied Zinc and balancing nutritional inputs are likely necessary for improving plant health, IF(AND(AM17>120, AM17<141),"Soil exchangeable Zinc is significant. This may limit availability of several other nutrients. Improve balance in the soil to allow more nutritional benefit and develop healthier turf ",IF(AM17>140,"Soil exchangeable Zinc is excessive. This may limit the availability of other beneficial nutrients and cause toxicity effects. Balance all nutrient inputs to allow for most benefit to the turf.

B:=IF(AND(AM18<121,AM18>79))," Soil exchangeable Boron is acceptable, IF(AND(AM18>60,AM18<80),"Soil exchangeable Boron is limiting. Consider regular soil soluble Boron applications and correct imbalances with soil applied and foliar nutrients, IF(AM18<60,"Soil exchangeable Boron is very low. Regular applications of soil soluble and foliar-applied Boron and balancing nutritional inputs are likely necessary for improving plant health, IF(AND(AM18>120, AM18<141),"Soil exchangeable Boron is significant. This may limit availability of several other nutrients. Improve balance in the soil to allow more nutritional benefit and develop healthier turf. ",IF(AM 18>140,"Soil exchangeable Boron is excessive. This may limit the availability of other beneficial nutrients and cause toxicity effects. Balance all nutrient inputs to allow for most benefit to the turf.

Na=IF(AND(AM19<121,AM19>79),"Soil exchangeable Sodium is acceptable, IF(AND(AM19>60,AM19<80),"Soil exchangeable Sodium is acceptable, IF(AM19<60,"Soil exchangeable Sodium is acceptable, IF(AND(AM19>120, AM19<141),"Soil exchangeable Sodium is significant. This may limit availability of beneficial nutrients. Improve drainage and supply balance of beneficial nutrients often. ",IF (AM19>140,"Soil exchangeable Sodium is excessive. This limits availability of beneficial nutrients. Improve drainage and supply balance of beneficial nutrients often.

Total Potential Salts:=IF(AND(AM20<121,AM20>79), "Total soil exchangeable salts is acceptable, IF(AND (AM20>60,AM20<80),"Total soil exchangeable salts is limiting. Consider balanced input of beneficial nutrients, IF(AM20<60,"Total soil exchangeable salts is very limiting. Consider balanced input of beneficial nutrients often with supplemental foliar feeding to correct deficiencies, IF(AND (AM20>120,AM20<141),"Total soil exchangeable salts is significant. This may limit availability of beneficial nutrients depending on the nutritional imbalances. Monitor balance of salts and correct. ",IF(AM20>140,"Total soil exchangeable salts is excessive. This may lead to deterioration of soil structure and quality. Improve drainage and monitor balance of nutrients. Consider organic amendments.

The available nutrients and salts logarithmic equations include the following.

N03:=IF(AND(A08<121,A08>79),"Soil available Nitrate is acceptable, IF(AND(A08>60,A08<80),"Soil available Nitrate is limiting. Consider foliar nitrogen applications routinely and build nitrogen reserves in soil while balancing other nutrients, IF(A08<60,"Soil available Nitrate is very low. Consider building nitrogen reserves in the soil from organic sources of N and apply nitrogen regularly at light rates foliarly to prevent deficiencies while balancing other nutrients, IF(AND(A08>120,A08<141),"Soil available Nitrate is significant. Consider applications of complex amino acids to utilize nitrogen and prevent excessive tissue growth while balancing other nutrients. ",IF(A08>140,"Soil available Nitrate is excessive. Regular applications of complex amino acids will help prevent succulent leaf growth. Limit nitrogen inputs and balance all other nutrients.

NH4:=IF(AND(A09<121,A09>79),"Soil available Ammonium is acceptable, IF(AND(A09>60,A09<80),"Soil available Ammonium is limiting. Consider foliar nitrogen applications routinely and build nitrogen reserves in soil while balancing other nutrients, IF(A09<60,"Soil available Ammonium is very low. Consider building nitrogen reserves in the soil from organic sources of N and apply nitrogen regularly at light rates foliarly to prevent deficiencies while balancing other nutrients, IF(AND(A09>120,A09<141), "Soil available Ammonium is significant. Consider applications of complex amino acids to utilize nitrogen and prevent excessive tissue growth while balancing other nutrients, IF(A09>140, Soil available Ammonium is excessive. Regular applications of complex amino acids will help prevent succulent leaf growth. Limit nitrogen inputs and balance all other nutrients.

P04:=IF(AND(A010<121,AOlO>79),"Soil available Phosphate is acceptable, IF(AND(A010>60,A010<80),"Soil available Phosphorus is limiting. Consider foliar P applications and correct imbalances with soil applied nutrients, IF(AO10<60,"Soil available Phosphorus is very low. Consider building Phosphorus reserves in the soil from various sources of P and apply Phosphorus regularly at light rates foliarly to prevent deficiencies, IF(AND(AO10>120, A010<141),"Soil available Phosphorus is significant. This may limit availability of other nutrients such as Calcium, Iron, Magnesium and Manganese. Improve balance in the soil to allow more nutritional benefit, IF(A010>140,"Soil available Phosphorus is excessive. This is likely limiting the availability of other beneficial nutrients such as Ca, Mg, Fe and Mn. Balance all nutrient inputs to allow for most benefit to the turf.

Ca:=IF(AND(AO11<121,AO11>79),"Soil available Calcium is acceptable, IF(AND(AO11>60,AO11<80),"Soil available Calcium is limiting. Consider foliar and soil soluble Calcium applications and correct imbalances with soil applied nutrients, IF(AO11<60,"Soil available Calcium is very low. Consider building reserves in the soil from bulk sources of Calcium and apply Calcium regularly at light rates foliarly and with soil soluble sources to prevent deficiencies, IF(AND(AO11>120,AO11<141),"Soil available Calcium is significant. This may limit availability of other nutrients. Improve balance in the soil to allow more nutritional benefit, IF(AO11>140,"Soil available Calcium is excessive. This is likely limiting the availability of other beneficial nutrients, particularly Phosphorus. Balance all nutrient inputs to allow for most benefit to the turf.

Mg:=IF(AND(A012<121,A012>79),"Soil available Magnesium is acceptable, IF(AND(A012>60,A012<80),"Soil available Magnesium is limiting. Consider soluble Magnesium applications and correct imbalances with soil applied nutrients, IF(A012<60,"Soil available Magnesium is very low. Consider building reserves in the soil from bulk sources of Magnesium and apply Magnesium regularly at light rates from soluble sources to prevent deficiencies, IF(AND (A012>120,A012<141),"Soil available Magnesium is significant. This may limit availability of other nutrients. Improve balance in the soil to allow more nutritional benefit, IF(A012>140,"Soil available Magnesium is excessive. This is likely limiting the availability of other beneficial nutrients, particularly Phosphorus and Calcium. Balance all nutrient inputs to allow for most benefit to the turf.

K:=IF(AND(A013<121,A013>79),"Soil available Potassium is acceptable IF(AND(A013>60,A013<80),"Soil available Potassium is limiting. Consider soluble Potassium applications and correct imbalances with soil applied nutrients, IF(A013<60,"Soil available Potassium is very low. Consider building reserves in the soil from granular sources of Potassium and apply Potassium regularly at light rates foliarly to prevent deficiencies, IF(AND(A013>120,A013<141),"Soil available Potassium is significant. This may limit availability of other base nutrients. Improve balance in the soil to allow more nutritional benefit, IF(A013>140,"Soil available Potassium is excessive. This is likely limiting the availability of other beneficial nutrients, particularly Calcium and Magnesium. Balance all nutrient inputs to allow for most benefit to the turf.

SO4:=IF(AND(AO14<121,AO14>79),"Soil available Sulfate is acceptable IF(AND(AO14>60,AO14<80),"Soil available Sulfate is limiting. Consider soluble Sulfate-based foliar applications and correct imbalances with soil applied nutrients, IF(AO14<60,"Soil available Sulfate is very low. Consider building reserves in the soil from granular sources of Sulfate-based products and apply Sulfate-based soluble products regularly at light rates foliarly to prevent deficiencies, IF(AND(AO14>120,AO14<141),"Soil available Sulfate is significant. This may limit efficient nitrogen utilization. Improve balance in the soil to allow more nutritional benefit, IF(AO14>140,"Soil available Sulfate is excessive. This is likely limiting the efficiency of nitrogen uptake and minor nutrient reactions. Balance all nutrient inputs to allow for most benefit to the turf.

B03:=IF(AND(AO15<121,AO15>79),"Soil available Boron is acceptable, IF(AND(AO15>60,AO15<80),"Soil available Boron is limiting. Consider soluble Boron foliar applications with a biostimulant or minor nutrient complex, IF(AO15<60,"Soil available Boron is very low. Consider applying Boron-containing soluble products regularly at light rates foliarly to prevent deficiencies IF(AND(AO15>120, AO15<141),"Soil available Boron is significant. This may lead to toxicity effects. Balance nutrients to improve plant health, IF(AO15>140,"Soil available Boron is excessive. This is likely to cause toxicity effects. Consider applying a complex humic acid product or amino acid complex to help utilize nutrients effectively. Balance all nutrient inputs to allow for most benefit to the turf.

Na:=IF(AND(AO16<121,AO16>79),"Soil available Sodium is acceptable, IF(AND(AO16>60,AO16<80),"Soil available Sodium is acceptable, IF(AO16<60,"Soil available Sodium is acceptable, IF(AND(AO16>120,AO16<141), Soil available Sodium is significant. This may lead to nutritional deficiencies and chlorotic turf. Improve drainage and balance nutritional inputs to offset Sodium regularly, IF(AO16>140, "Soil available Sodium is excessive. This is likely to cause toxicity effects and significant nutrient deficiencies. Improve drainage and replenish beneficial nutrients regularly. Balance all nutrient inputs to allow for most benefit to the turf.

Cl:=IF(AND(AO17<121,AO17>79),"Soil available Chlorine is acceptable ,IF(AND(AO17>60,AO17<80),"Soil available Chlorine is acceptable, IF(AO17<60,"Soil available Chlorine is acceptable, IF(AND(AO17>120,AO17<141), Soil available Chlorine is significant. This may lead to nutritional deficiencies and chlorotic turf. Improve drainage and balance nutritional inputs to offset Chlorine regularly. IF(AO17>140, "Soil available Chlorine is excessive. This is likely to cause toxicity effects and significant nutrient deficiencies. Improve drainage and replenish beneficial nutrients regularly. Balance all nutrient inputs to allow for most benefit to the turf.

HC03:=IF(AND(AO18<121,AO18>79),"Soil available Bicarbonates is acceptable, IF(AND(AO18>60,AO18<80), "Soil available Bicarbonates is acceptable, IF(AO18<60,"Soil available Bicarbonates is acceptable, IF(AND(AO18>120, AO18<141),"Soil available Bicarbonates is significant. This may lead to nutritional deficiencies and precipitated salts in the soil. Balance nutritional inputs to offset and limit Bicarbonates regularly, IF(AO18>140,"Soil available Bicarbonates is excessive. This is likely to cause significant nutrient deficiencies. Improve drainage and replenish beneficial nutrients regularly. Balance all nutrient inputs to allow for most benefit to the turf.

Total Available Salts:=IF(AND(AO19<121,AO19>79), "Total available salts is acceptable IF(AND(AO19>60, AO19<80), Total available salts is limiting. Consider balanced inputs of beneficial nutrients to maintain a healthy level of nutrition, IF(AO19<60,"Total available salts is very low. Regular applications of balanced soluble nutrition is necessary for healthy and strong turf conditions, IF(AND (AO19>120,AO19<141), Total available salts is significant. Maintain balance of nutrients and consider a complex amino acid product to help utilize nutrition effectively, IF(AO19>140,"Total available salts is excessive. Maintain healthy drainage qualities to move salts readily through the soil. Maintain balanced nutrition for healthy turf conditions.

The Potential Base Saturation logarithmic equations include the following.

Calcium PBS:=IF(AND(AQ8<121,AQ8>79),"% Base Saturation of Calcium is acceptable, IF(AND(AQ8>60, AQ8<80),"% Base saturation of Calcium is limiting. Consider bulk applications of Calcium and regular soluble inputs to improve availability if base levels are low, IF(AQ8<60,"% Base saturation of Calcium is very limiting. Bulk applications of Calcium are likely necessary to improve soluble Calcium availability if base levels are low. Regular applications of soluble Calcium will provide benefit to nutritional balancing, IF(AND(AQ8>120,AQ8<141), % Base saturation of Calcium is significant in relation to other base nutrients. Check levels of all bases to identify balance imperfections and supply soluble Calcium to improve soil nutritional health. IF(AQ8>140,"% Base saturation of Calcium is excessive in relation to other bases. Correct imbalances with soluble applications to improve soil nutritional health.

Magnesium PBS:=IF(AND(AQ9<121,AQ9>79),"% Base Saturation of Magnesium is acceptable, IF(AND(AQ9>60, AQ9<80),"% Base saturation of Magnesium is limiting. Consider granular applications of Magnesium and regular soluble inputs to improve availability if bases are low, IF(AQ9<60,"% Base saturation of Magnesium is very limiting. Granular and soluble applications of Magnesium are likely necessary to improve soluble Magnesium availability if bases are low, IF(AND(AQ9>120,AQ9<141), % Base saturation of Magnesium is significant in relation to other base nutrients. Check levels of all bases to identify balance imperfections and supply soluble sources to improve soil health. IF(AQ9>140,"% Base saturation of Magnesium is excessive in relation to other bases. Correct imbalances with soluble products to improve soil nutritional health.

Potassium PBS:=IF(AND(AQ10<121,AQ10>79),"% Base Saturation of Potassium is acceptable, IF(AND (AQ10>60,AQ10<80),"% Base saturation of Potassium is limiting. Consider granular applications of Potassium and regular soluble inputs to improve availability if base levels are low, IF(AQ10<60,"% Base saturation of Potassium is very limiting. Granular and foliar applications of Potassium are likely necessary to improve soluble Potassium availability if base levels are low, IF(AND(AQ10>120,AQ10<141),"% Base saturation of Potassium is significant in relation to other base nutrients. Check levels of all bases to identify balance imperfections, IF(AQ10>140,"% Base saturation of Potassium is excessive in relation to other bases. Correct imbalances with soluble applications to improve soil nutritional health.

Sodium PBS:=IF(AND(AQ11<121,AQ11>79),"% Base Saturation of Sodium is acceptable, IF(AND(AQ11>60, AQ11<80),"% Base Saturation of Sodium is acceptable, IF(AQ11<60,"% Base Saturation of Sodium is acceptable, IF(AND(AQ11>120,AQ11<141),"% Base saturation of Sodium is significant in relation to other base nutrients. Check levels of all bases to identify balance imperfections and increase beneficial base levels to offset Sodium. Improve drainage, IF(AQ11>140, % Base saturation of Sodium is excessive in relation to other bases. Correct imbalances to improve soil nutritional health and increase beneficial base levels to offset Sodium. Improve drainage.

Hydrogen PBS:=IF(AND(AQ12<121,AQ12>79),"% Base Saturation of Hydrogen is acceptable, IF(AND (AQ12>60,AQ12<80),"% Base Saturation of Hydrogen is acceptable, IF(AQ12<60,"% Base Saturation of Hydrogen is acceptable, IF(AND(AQ12>120,AQ12<141),"% Base saturation of Hydrogen is significant in relation to other base nutrients. Check levels of all bases to identify balance imperfections and supply beneficial bases to occupy exchange sites and improve soil solution levels, IF(AQ12>140,"% Base saturation of Hydrogen is excessive in relation to other bases. Check levels of all bases to identify balance imperfections and supply beneficial bases to occupy exchange sites and improve soil solution levels.

The available base saturation logarithmic equations include the following.

Available Ca Base %:=IF(AND(AU8<121,AU8>79), "Available base % of Calcium is adequate, IF(AND (AU8>60,AU8<80),"Available base % of Calcium is limiting. Adjust balance of available bases with soluble sources to correct, IF(AU8<60,"Available base % of Calcium is very low. Routine soluble applications of Calcium are likely necessary for proper balancing of base nutrients. Check all base nutrient levels to improve proper balance, IF(AND (AU8>120,AU8<141),"Available base % of Calcium is significant in relation to other bases. Check all levels and use soluble sources to correct balance, IF(AU8>140,"Available base % of Calcium is excessive compared to other base nutrients. Check all base nutrient levels and correct regularly with soluble sources.

Available Mg Base %:=IF(AND(AU9<121,AU9>79), "Available base % of Magnesium is adequate IF(AND (AU9>60,AU9<80),"Available base % of Magnesium is limiting. Adjust balance of available bases with soluble sources to correct IF(AU9<60,"Available base % of Magnesium is very low. Routine soluble applications of Magnesium are likely necessary for proper balancing of base nutrients. Check all base nutrient levels to improve proper balance, IF(AND (AU9>120,AU9<141),"Available base % of Magnesium is significant in relation to other bases. Check all levels and use soluble sources to correct balance, IF(AU9>140,"Available base % of Magnesium is excessive compared to other base nutrients. Check all base nutrient levels and correct regularly with soluble sources.

Available K Base %:=IF(AND(AU10<121,AU10>79), "Available base % of Potassium is adequate IF(AND (AU10>60,AU10<80),"Available base % of Potassium is limiting. Adjust balance of available bases with soluble sources to correct, IF(AU10<60,"Available base % of Potassium is very low. Routine soluble applications of Potassium are likely necessary for proper balancing of base nutrients. Check all base nutrient levels to improve proper balance. IF{AND{AU10>120,AU10<141),"Available base % of Potassium is significant in relation to other bases. Check all levels and use soluble sources to correct balance, IF{AU10>140,"Available base % of Potassium is excessive compared to other base nutrients. Check all base nutrient levels and correct regularly with soluble sources.

Available Na Base %:=IF{AND{AU11<121,AU11>79), "Available base % of Sodium is adequate IF{AND{AU11>60,AU11<80),"Available base % of Sodium is adequate, IF{AU11<60,"Available base % of Sodium is adequate, IF{AND{AU11>120,AU11<141), "Available base % of Sodium is significant in relation to other bases. this will likely lead to plant and soil health issues. Check all levels and use soluble sources to correct base nutrient balance, IF{AU11>140,"Available base % of Sodium is excessive compared to other base nutrients. This will likely lead to long term plant stress if beneficial base nutrient percentages are not increased. Correct imbalances with routine applications of soluble base nutrients.

The ratio analyses logarithmic equations include the following.

N03/NH4:=IF{AND{AW8<121,AW8>79),"Available ratio of Nitrate to Ammonium is acceptable, IF{AND{AW8>60,AW8<80),"Available ratio of Nitrate to Ammonium is low. Utilizing more Nitrate-based soil and foliar applications will aid in efficient Nitrogen utilization, IF{AW8<60,"Available ratio of Nitrate to Ammonium is very low. Increase Nitrate based nutrition at light and frequent levels to correct ratio and improve nitrogen utilization, IF{AND{AW8>120,AW8<141),"Available ratio of Nitrate to Ammonium is significant. Balance applications of Ammonium and Nitrate fertilizers to correct balance on a routine basis, IF{AW8>140,"Available ratio of Nitrate to Ammonium is excessive. Improve Nitrogen balance through routine and light nutritional applications.

Ca/Mg:=IF{AND{AW9<121,AW9>79),"Available ratio of Calcium to Magnesium is acceptable IF{AND{AW9>60, AW9<80), Available ratio of Calcium to Magnesium is low. Check all base nutrient levels and improve levels of Calcium with soluble sources to offer more efficient base nutrient availability, IF{AW9<60,"Available ratio of Calcium to Magnesium is very low. Correct balance of all base nutrients to improve availability of several nutrients, and utilize soluble sources of Calcium routinely. IF{AND{AW9>120, AW9<141),"Available ratio of Calcium to Magnesium is significant. Balance applications of Calcium and Magnesium fertilizers on a routine basis, IF{AW9>140,"Available ratio of Calcium to Magnesium is excessive. This will limit availability of several nutrients. Improve Magnesium balance and availability through routine soluble nutritional applications.

N/K: IF{AND{AW10<121,AW10>79),"Available ratio of Nitrogen to Potassium is acceptable IF{AND{AW10>60, AW10<80),"Available ratio of Nitrogen to Potassium is low. Check levels of K and balance foliar applications of Nitrogen and Potassium regularly. ",IF{AW10<60,"Available ratio of Nitrogen to Potassium is very low. Check levels of K to insure excess is not present. Balance Nitrogen inputs to allow for consistent delivery of N.",IF{AND{AW10>120, AW10<141), Available ratio of Nitrogen to Potassium is high. Monitor N and K inputs closely, IF{AW10>140,"Available ratio of Nitrogen to Potassium is excessive. If K levels are high this could lead to rapid moisture loss from leaf tissue and succulent growth. Monitor N and K inputs closely and consider an amino acid complex to offset excessive growth.

Ca/P: IF{AND{AW11<121,AW11>79),"Available ratio of Calcium to Phosphorus is acceptable, IF{AND{AW11>60,AW11<80),"Available ratio of Calcium to Phosphorus is low. This will limit the routine uptake of Calcium and may lead to unavailability of additional nutrients. Consider routine soluble Calcium applications and humic acids to free up nutrients. ",IF{AW11<60,"Available ratio of Calcium to Phosphorus is very low. Check levels of each and utilize soluble sources routinely to correct balances and free up several nutrients. ",IF{AND{AW11>120, AW11<141),"Available ratio of Calcium to Phosphorus is high. This will likely lead to unavailability of P. Correct balance with soluble sources of each, IF{AW11>140,"Available ratio of Calcium to Phosphorus is very high. Inadequate P levels may seriously hinder turf performance. Check levels and adjust balances with regular soluble sources of nutrition through the soil and foliage. (Na—CI—HC03)/Total Available Salts:=IF(AND(AW12<121,AW12>79),"Available ratio of Na—CI—HC03 to total available salts is acceptable, IF(AND(AW12>60,AW12<80),"Available ratio of Na—CI—HC03 to total available salts is acceptable. ",IF(AW12<60,"Available ratio of Na—CI—HC03 to total available salts is acceptable. ",IF(AND(AW12>120,AW12<141),"Available ratio of Na—CI—HC03 to total available salts is high. This may lead to several nutritional deficiencies and plant stress. Improve levels of soluble beneficial nutrients regularly and address water source if possible, IF(AW12>140,"Available ratio of Na—CI—HC03 to total available salts is excessive. This will likely lead to nutritional deficiencies, loss of root mass and chlorosis. Improve beneficial nutrient and base levels through frequent soluble applications of balanced nutrition.

Ca/HC03:=IF(AND(AW13<121,AW13>79),"Available ratio of Calcium to Bicarbonates is acceptable, IF(AND (AW13>60,AW13<80),"Available ratio of Calcium to Bicarbonates is low. This will lead to precipitation of insoluble Calcium. Improve Calcium levels through routine soluble soil applications. ",IF(AW13<60,"Available ratio of Calcium to Bicarbonates is very low. This will lead to precipitation of insoluble Calcium. Improve Calcium levels through routine soluble soil applications, IF(AND(AW13>120,AW13<141), "Available ratio of Calcium to Bicarbonates is acceptable, IF(AW13>140,"Available ratio of Calcium to Bicarbonates is acceptable.

Mg/HC03:=IF(AND(AW14<121,AW14>79),"Available ratio of Magnesium to Bicarbonates is acceptable, IF(AND (AW14>60,AW14<80),"Available ratio of Magnesium to Bicarbonates is low. This will lead to precipitation of insoluble Magnesium. Improve Magnesium levels through routine soluble soil applications. ",IF(AW14<60,"Available ratio of Magnesium to Bicarbonates is very low. This will lead to precipitation of insoluble Magnesium. Improve Magnesium levels through routine soluble soil applications. IF(AND(AW14>120,AW14<141), Available ratio of Magnesium to Bicarbonates is acceptable, IF(AW14>140,"Available ratio of Magnesium to Bicarbonates is acceptable.

K/CI:=IF(AND(AW15<121,AW15>79),"Available ratio of Potassium to Chlorine is acceptable, IF(AND(AW15>60, AW15<80),"Available ratio of Potassium to Chlorine is low. This will hinder the turfs ability to offset stress. Improve K levels with soluble soil and foliar applications, IF(AW15<60, "Available ratio of Potassium to Chlorine is very low. This will hinder the turfs ability to offset stress and will likely show droughty appearances. Improve K levels with soluble soil and foliar applications at light and frequent rates, IF(AND (AW15>120,AW15<141),"Available ratio of Potassium to Chlorine is acceptable, IF(AW15>140,"Available ratio of Potassium to Chlorine is acceptable.

Total Potential/Total Available Salts:=IF(AND (AW16<121,AW16>79),"Total Potential to Available salts is acceptable, IF(AND(AW16>60,AW16<80),"Total Potential to Available salts is low. Monitor Potential levels closely and build buffer of nutrients through soil applied granular sources when cultural practices are performed. ",IF(AW16<60,"Total Potential to Available salts is very low. Improve bulk nutrient applications to the soil whenever the subsurface is exposed such as during core aerification, IF(AND(AW16>120, AW16<141),"Total Potential to Available salts ratio is high. Utilize strong humic acid products to free up buffered nutrients. Balance nutrients based on Available levels, IF(AW16>140,"Total Potential to Available salts ratio is very high. Utilize strong humic acid products to free up buffered nutrients. Balance nutrients based on Available levels routinely with soil soluble and foliar-applied sources.

The legend of the variables is as follows below.

pH: a scientific logarithmic measurement of the free hydrogen ions in solution to determine acidic (more H ions) or alkaline (fewer H ions) conditions. A pH of 7.0 is neutral where there are equal parts of Hydrogen ions to hydroxyl (OH) ions.

Buffer pH: the pH of the soil to resist change in pH and is typically calculated for acidic soils.

OM %: organic matter percentage based on Loss On Ignition technology otherwise known as LOI which is a process where the soil sample is dried in an oven and then heated to a temperature that burns off the organic matter. The soil is then weighed again to understand the amount of organic matter that was present before being burned off.

CEC: Cation Exchange Capacity which is a lab measurement of the ability of a soil to hold cations which are positively charged ions.

Texture: The standard scientific measurement of a soil's textural makeup of the key soil particle size percentages. The three soil components are sand, silt and clay.

Sand, Silt and Clay: The percentages of each of these in the soil sample calculated by the lab.

Saturation %: A lab measurement of how many equal parts of water it takes to saturate equal parts of soil.

SAR: (Sodium adsorption ratio) which is a lab measurement of how sodium ions compare to the base cations of Calcium and Magnesium.

EC (1:1 Sol Salts): Electrical conductivity measured in decisiemens/meter (dS/m) of equal parts of soil to distilled water where the conductivity is measured in the solution that freely flows through the soil.

EC Paste Extract: Electrical conductivity measured in decisiemens/meter (dS/m) of a saturated soil where the soil is allowed to remain saturated for several hours. The EC is then measured directly from the soil paste sample. i.Exchangeable Report (Exchangeable salts are "mined" using various acid extractants used to "pull" salts off of chemically attractive sites within the soil. It is a measurement of the potential salts that can be derived from that soil over time but not necessarily what the plant sees easily in solution): N03: Nitrate, P: Phosphorus, Ca: Calcium, Mg: Magnesium, K: Potassium, S: Sulfur, Fe: Iron, Mn: Manganese, Zn: Zinc, Cu: Copper k. B: Boron, Na: Sodium, TOT POT SALTS: All of the above exchangeable salts added together Extractable (Available) Report (derived from filtered distilled water through the soil to see the salts that easily go into solution for plant uptake): N03: Nitrate, NH4: Ammonium, P04: Phosphate, Ca: Calcium, Mg: Magnesium, K: Potassium, S04: Sulfate, B03: Borate, Na: Sodium, Cl: Chlorine (Chlorides), HC03: Bicarbonate, TOT AVAIL SALTS: All of the above extractable salts added together.

Base Saturation % Report: Ca: Measurement of the % of Calcium to the total of Calcium, Magnesium, Potassium, Sodium and Hydrogen in the soil based on exchangeable (potential) salts; Mg: Measurement of the % of Magnesium to the total of Calcium, Magnesium, Potassium, Sodium and Hydrogen in the soil based on exchangeable (potential) salts; K: Measurement of the % of Potassium to the total of Calcium, Magnesium, Potassium, Sodium and Hydrogen in the soil based on exchangeable (potential) salts; Na: Measurement of the % of Sodium to the total of Calcium, Magnesium, Potassium, Sodium and Hydrogen in the soil based on exchangeable (potential) salts; H: Measurement of the % of Hydrogen to the total of Calcium, Magnesium, Potassium, Sodium and Hydrogen in the soil based on exchangeable (potential) salts.

Potential Base % Report: Ca: Measurement of the % of Calcium to the total of Calcium, Magnesium, Potassium, and Sodium in the soil based on exchangeable (potential) salts; Mg: Measurement of the % of Magnesium to the total of Calcium, Magnesium, Potassium, and Sodium in the soil based on exchangeable (potential) salts; K: Measurement of the % of Potassium to the total of Calcium, Magnesium, Potassium, and Sodium in the soil based on exchangeable (potential) salts; Na: Measurement of the % of Sodium to the total of Calcium, Magnesium, Potassium, and Sodium in the soil based on exchangeable (potential) salts.

Available Base % Report: Ca: Measurement of the % of Calcium to the total of Calcium, Magnesium, Potassium, and Sodium in the soil based on extractable (available) salts; Mg: Measurement of the % of Magnesium to the total of Calcium, Magnesium, Potassium, and Sodium in the soil based on extractable (available) salts; K: Measurement of the % of Potassium to the total of Calcium, Magnesium, Potassium, and Sodium in the soil based on extractable (available) salts; Na: Measurement of the % of Sodium to the total of Calcium, Magnesium, Potassium, and Sodium in the soil based on extractable (available) salts.

Ratio Report: N03/NH4: Ratio of available nitrate to ammonium nitrogen; Ca/Mg: Ratio of available Calcium to Magnesium; N/K: Ratio of available Nitrogen to Potassium; Ca/P: Ratio of available Calcium to Phosphorus; (Na—CI—HC03)/Tot: Ratio of the total of Sodium, Chlorine and Bicarbonates to the total available salts in solution; Ca/HC03: Ratio of available Calcium to Bicarbonates; Mg/HC03: Ratio of available Magnesium to Bicarbonates h. K/CI: Ratio of available Potassium to Chlorides; TOT Potential/TOT Available Salts: Ratio of the total potential exchangeable salts to total available extractable salts.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A method for analyzing soil conditions for a land area, the method comprising:
   analyzing at least one soil sample for a land area, the soil sample ranging from 3 inches to 4 inches and including a cap;
   generating a plurality of variables for the at least one analyzed soil sample;
   applying a logarithmic equation to each of the plurality of variables to generate a plurality of logarithmic values for the at least one soil sample;
   monitoring the land area utilizing a system comprising a plurality of soil sensors positioned in an upper soil area and a lower soil area, at least one transmitter and a processing engine in wireless communication with the transmitter for receiving a plurality of wireless transmissions from each of the plurality of soil sensors wherein each of the plurality of wireless transmissions corresponds to at least one variable of the plurality of variables.

2. The method according to claim 1 wherein the plurality of variables comprises pH, buffer pH, organic matter percentage, texture, sand, silt, clay, saturation percentage, cation exchange capacity, sodium adsorption ratio, electrical conductivity soluble salts and electrical conductivity paste extract salts.

3. The method according to claim 1 wherein the plurality of variables comprises a plurality of acid exchangeable nutrients and a plurality of free-extractable nutrients.

4. The method according to claim 3 wherein the plurality of variables for the plurality of acid exchangeable nutrients comprises nitrate, phosphorous, calcium, magnesium, potassium, sulfur, iron, manganese, zinc, copper, boron and sodium.

5. The method according to claim 3 wherein the plurality of variables for the plurality of free extractable nutrients comprises nitrate, ammonium nitrogen, phosphate, calcium, magnesium, potassium, sulfate, borate, sodium, chlorine and bicarbonate.

6. The method according to claim 1 wherein the plurality of variables comprises a plurality of base saturation percentages, a plurality of potential base percentages, and a plurality of available base percentages.

7. The method according to claim 6 wherein the plurality of variables for the plurality of base saturation percentages comprises calcium base saturation percent, magnesium base saturation percent, potassium base saturation percent, sodium base saturation percent, and hydrogen base saturation percent.

8. The method according to claim 6 wherein the plurality of variables for the plurality of potential base percentages comprises calcium potential base percent, magnesium potential base percent, potassium potential base percent, and sodium potential base percent.

9. The method according to claim 6 wherein the plurality of variables for the plurality of available base percentages comprises calcium available base percent, magnesium available base percent, potassium available base percent, and sodium available base percent.

10. The method according to claim 1 wherein each of the plurality of logarithmic values is a value between 0 and 200.

11. The method according to claim 10 wherein the optimal value for each of the plurality of logarithmic values is a value between 80 and 120.

12. The method according to claim 1 further comprising:
   generating a plurality of ratios of variables for the at least one analyzed soil sample; and
   applying a logarithmic equation to each of the plurality of ratios of variables to generate a plurality of logarithmic ratio values for the at least one soil sample.

13. The method according to claim 12 wherein the plurality of ratios of variables comprises available nitrate to ammonium nitrogen, available calcium to magnesium, available nitrogen to potassium, available calcium to phosphorus, total of sodium, chlorine and bicarbonates to the total available salts in solution, available calcium to bicarbonates, available magnesium to bicarbonates, available potassium to chlorides, and total potential exchangeable salts to total available extractable salts.

14. The method according to claim 13 wherein each of the plurality of logarithmic ratio values is a value between 0 and 200.

15. A method for analyzing soil conditions for a land area, the method comprising:
   analyzing a plurality of soil samples for a land area, each of the plurality of soil samples ranging from 3 inches to 4 inches and including a cap;

generating a plurality of variables and a plurality of ratios of variables for the analyzed plurality of soil samples;

applying a logarithmic equation to each of the plurality of variables and each of the plurality of ratios of variables to generate a plurality of logarithmic values for the plurality of soil samples, wherein the logarithmic equation is $$\text{logarithmic value} = \text{slope} * \text{LOG}(\text{actual variable value}/\text{optimal variable value}) + \text{scale; and}$$

monitoring the land area utilizing a system comprising a plurality of soil sensors positioned in an upper soil area and a lower soil area, at least one transmitter and a processing engine in wireless communication with the transmitter for receiving a plurality of wireless transmissions from each of the plurality of soil sensors wherein each of the plurality of wireless transmissions corresponds to at least one variable of the plurality of variables.

16. The method according to claim 15 wherein the plurality of variables comprises pH, buffer pH, organic matter percentage, texture, sand, silt, clay, saturation percentage, cation exchange capacity, sodium adsorption ratio, electrical conductivity soluble salts and electrical conductivity paste extract salts.

17. The method according to claim 15 wherein the plurality of variables comprises a plurality of acid exchangeable nutrients and a plurality of free-extractable nutrients.

18. The method according to claim 17 wherein the plurality of variables for the plurality of acid exchangeable nutrients comprises nitrate, phosphorous, calcium, magnesium, potassium, sulfur, iron, manganese, zinc, copper, boron and sodium.

19. The method according to claim 17 wherein the plurality of variables for the plurality of free extractable nutrients comprises nitrate, ammonium nitrogen, phosphate, calcium, magnesium, potassium, sulfate, borate, sodium, chlorine and bicarbonate.

20. A method for analyzing soil conditions for a land area, the method comprising:

analyzing at least one soil sample for a land area;

generating a plurality of variables for the at least one analyzed soil sample;

applying a scaling function to each of the plurality of variables to generate a plurality of scaled variable values for the at least one soil sample, wherein such that for each variable value $V1, \ldots Vn$, then $S1=f1(V1) \ldots Sn=fn(Vn)$, wherein $S1 \ldots Sn$ are scaled variable values and $f1 \ldots fn$ are functions specific to each variable $V1 \ldots Vn$; and monitoring the land area utilizing a system comprising a plurality of soil sensors positioned in an upper soil area and a lower soil area, at least one transmitter and a processing engine in wireless communication with the transmitter for receiving a plurality of wireless transmissions from each of the plurality of soil sensors wherein each of the plurality of wireless transmissions corresponds to at least one variable of the plurality of variables.

* * * * *